United States Patent [19]

Huck et al.

[11] 4,392,860

[45] Jul. 12, 1983

[54] DISPOSABLE WOUND DRAINAGE DEVICE

[75] Inventors: Charles M. Huck, Oldwick; John E. Studer, Flemington, both of N.J.; Philip H. Sauer, Indian Rocks Beach, Fla.

[73] Assignee: Howmedica, Inc., New York, N.Y.

[21] Appl. No.: 214,571

[22] Filed: Dec. 8, 1980

Related U.S. Application Data

[63] Continuation of Ser. No. 2,610, Jan. 11, 1979, abandoned.

[51] Int. Cl.³ .............................................. A61M 1/00
[52] U.S. Cl. ...................................................... 604/212
[58] Field of Search ............... 128/275, 276, 277, 278, 128/297; 138/30; 141/7, 8, 65, 66; 15/347, 353; 417/394, 395, 472; 604/212, 213, 214, 216, 217, 146, 256

[56] References Cited

U.S. PATENT DOCUMENTS

| | | | |
|---|---|---|---|
| 2,597,059 | 5/1952 | Bitzer | 417/395 |
| 3,084,691 | 4/1963 | Stoner | 128/278 |
| 3,111,145 | 11/1963 | Kerns | 128/278 |
| 3,556,101 | 1/1971 | Economou | 128/277 |
| 3,654,964 | 4/1972 | Mercier | 138/30 |
| 3,809,086 | 5/1974 | Schachet | 128/278 |
| 3,843,016 | 10/1974 | Bornhorst et al. | 220/306 |
| 3,845,765 | 11/1974 | Ikeda | 128/277 |
| 3,889,677 | 6/1975 | Nehring | 128/278 |
| 3,931,834 | 1/1976 | Caillet | 138/30 |
| 3,945,392 | 3/1976 | Deaton et al. | 128/277 |
| 3,965,902 | 6/1976 | Reilly et al. | 128/276 |
| 3,989,046 | 11/1976 | Pannier, Jr. et al. | 128/276 |
| 4,013,076 | 3/1976 | Puderbaugh | 128/276 |
| 4,022,209 | 5/1977 | Nehring | 128/278 |
| 4,058,123 | 11/1977 | May | 128/278 |
| 4,073,294 | 2/1978 | Stanley et al. | 128/278 |
| 4,085,751 | 4/1978 | Dodge | 128/275 |
| 4,111,204 | 9/1978 | Hessel | 128/276 |
| 4,112,947 | 9/1978 | Nehring | 128/278 |

FOREIGN PATENT DOCUMENTS

| | | |
|---|---|---|
| 53-196 | 12/1977 | Japan . |
| 1395799 | 3/1975 | United Kingdom . |
| 1400139 | 7/1975 | United Kingdom . |
| 1404959 | 9/1975 | United Kingdom . |
| 1435771 | 3/1976 | United Kingdom . |
| 1435772 | 3/1976 | United Kingdom . |
| 1480144 | 7/1977 | United Kingdom . |
| 1485279 | 9/1977 | United Kingdom . |
| 1524375 | 9/1978 | United Kingdom . |
| 2039745 | 8/1980 | United Kingdom ................ 128/278 |

OTHER PUBLICATIONS

"Bellows" Websters Seventh New Collegiate Dictionary, G. C. Thomson Co., Springfield, Mass., 1963, p. 79.

Primary Examiner—Richard J. Apley
Assistant Examiner—J. L. Kruter

[57] ABSTRACT

A device for removing fluids from a wound. The device includes a housing having therein an expandable and collapsible passive member which divides the interior of the housing into a first and a second chamber. A vacuum is applied to the second chamber to draw the passive member so as to increase the volume of the first chamber and create a negative pressure therein. Conventional wound tubing connected to the first chamber permits fluids to be drawn from the wound into the first chamber. In one exemplary embodiment a bellows is placed in communication with the second chamber.

14 Claims, 3 Drawing Figures

DISPOSABLE WOUND DRAINAGE DEVICE

This is a continuation of application Ser. No. 002,610, filed Jan. 11, 1979, now abandoned.

TECHNICAL FIELD

This invention relates to suction devices and more particularly to an improved device for automatic removal of fluids from a wound.

BACKGROUND ART

The use of suction devices to remove body fluids from a wound is known to the art. Such devices are employed to reduce or remove the body fluids which normally collect at a wound site after surgery.

Body fluids which collect as a wound, if left to remain especially in a closed wound, may cause complications in the healing process and thereby reduce the chance of a successful convalescence. Moreover, not only will a dry wound area accelerate the healing stage but will also promote cicatrization.

Known typical suction devices are both disclosed and illustrated in U.S. Pat. No. 3,809,086 to Schachet et al.; U.S. Pat. No. 3,845,765 to Ikeda; U.S. Pat. No. 3,889,677 to Nehring; U.S. Pat. No. 4,058,123 to May; U.S. Pat. No. 4,085,751 to Dodge; and U.S. Pat. No. 4,112,947 to Nehring.

The Schachet et al. patent is directed to a wound suction device including a vessel having therein an elastic sheet diaphragm which is sealed to the walls of the vessel. Movement of the diaphragm by a plate with an actuating means decreases the volume of the vessel which results in the creation of a suction force upon release of the actuating means. Provision is made to lock the actuator means in a position such that the resilient diaphragm remains displaced.

The device disclosed in the Ikeda patent includes a rigid outer vessel accommodating a flexible bag within. The interior of the flexible bag is in communication with the interior of the outer vessel whereby the interior of the flexible bag can be evacuated without its collapse as a result of the equalization of pressure within and without the bag.

The self-contained fluid evacuator of the Nehring '677 patent includes a substantially rigid container with an inflatable member therein. A means mounted on the container is provided for inflating the inflatable member. A valve means responsive to pressure differences between the inflation means and the inflatable member permits a higher rate of fluid flow into the inflatable member than without.

The May '123 and Nehring '947 patents disclose a combined irrigator and evacuator for bathing a wound with an irrigating solution and for removal of fluid therefrom. The apparatus comprises a rigid housing forming a chamber, a biased means dividing the chamber into two sections, a sealing means to prevent fluid flow between the sections, and access means to each section. Depression of the dividing means against its bias produces an increased volume in the irrigating section. Release of the solution from the irrigating section permits the dividing means under bias to return to its original position. During operation, the biasing means pumps fluid from the irrigation section to the wound thereby expanding the evacuation section to create a negative pressure and cause fluid flow therein. A selective rate control flow means provides for simultaneous expulsion of solution from the irrigation section and the admission of fluid from the wound into the evacuation section. Preferably th dividing means is a resilient diaphragm.

The Dodge patent discloses a drainage apparatus including a fluid drainage collection chamber with a liquid seal chamber disposed therein and above the collection chamber. An opening in the upper wall of the liquid seal chamber provides fluid communication between the two chambers. Fluid from the wound passes into the liquid seal chamber which has an initial quantity of fluid and evantually overflows from that chamber into the drainage collection chamber.

Although each of the above-mentioned patented devices is useful in varying degrees, they all suffer from disadvantages to some degree. The body fluids which are collected in typical suction devices sometimes contain a large number of viruses and other pathogenic microorganisms. Persons handling such drainage devices during collection and disposal of body fluids are thus exposed to a high risk of infection during use. Such exposure of the user to infection exists in the Schachet and Nehring '677 patents which disclose removal of the body fluids after collection.

Additionally, suction drainage devices wherein the suction means can communicate with the ambient and also with the collection chamber permit possible contamination of the wound by entry of bacteria and the like along the suction-evacuation flow. The Ikeda and Dodge patents both disclose devices wherein communication between the suction means and the collection chamber is possible thus permitting contamination of the wound.

Moreover, some typical known suction devices possess either complicated or specially required structure which not only increases the cost of construction but also makes operation difficult. The Schachet, May, and Nehring '947 patents disclose multiple-component biasing means. Each of these along with the Nehring '677 patent also disclose a preferred elastomeric member which upon returning to its original form increases the volume of the collection chamber to produce a negative pressure therein. Eventual fatigue of these elastomeric members further decreases the reliability of such devices.

The Ikeda and Dodge patents disclose devices generally limited to upright operation since fluids therein may otherwise gravitationally spill from chambers disposed within.

DISCLOSURE OF INVENTION

The device of the present invention is intended to improve over the apparatus discussed above and to overcome the limitations found therein. The device of the present invention is designed to provide a suction means which is isolated from the collected body fluids to prevent possible contamination of the wound. The device is also designed to permit use of a remote suction source capable of providing whatever degree of suction is required. In an alternative embodiment, the device can be used with a directly attachable suction source, preferably a bellows pump, which provides a portable device free of the limitations of a fixed suction means. The device is economically designed to permit upon separation of the vacuum source total discarding after collection of body fluids to be drained from the wound thereby reducing the danger of user infection.

The device of the present invention comprises a housing with side walls and at least one end wall at one end thereof. Inside the housing an expandable and collapsible passive member that is airtight and watertight is sealingly connected at its periphery to the side wall of the housing. Thereby the housing is divided into a first and a second chamber wherein the first chamber is contiguous with the end wall. The passive member is substantially expanded toward the end wall and substantially conforms to the inside of the side walls of the housing. A means is provided for drawing the passive member toward the other end of the housing thereby increasing the volume of the first chamber and creating a negative pressure within the first chamber whereby fluids may be removed from a wound.

In one exemplary embodiment of the present invention, the passive member is sealed at its periphery along the edges of the other end of the housing and a plate member is affixed to the other end of the housing to seal the second chamber. A remote suction means is attached to a hollow tube integral with the plate member and communicating with the second chamber. Upon application of a suction through the plate member tube, the passive member collapses into the second chamber thereby increasing the volume of the first chamber and creating a negative pressure therein. A hollow tube integral with the end wall and communicating with the first chamber is connected to conventional wound tubing that at its one end is disposed adjacent a wound thereby permitting fluids to be drawn into the first chamber.

In an alternative exemplary embodiment, an elastic bellows is connected to the plate member to provide a portable and hand operated suction means. A valve means permits discharge of the air within the bellows into the ambient upon compression while simultaneously preventing entry into the second chamber. Expansion of the bellows then provides suction to the second chamber. Consequently, subsequent recharging of the bellows is permitted without adversely affecting the level of negative pressure then within the second chamber.

Accordingly, it is an object of the present invention to provide a wound drainage device having a suction means isolated from the collected body fluids to provide contamination free evacuation of the wound.

Another object of the present invention is to provide a wound drainage device that permits infection free operation by the user.

Yet another object of the present invention is to provide a wound drainage device that is inexpensive and totally discardable.

Still yet another object is to provide a wound drainage device that is simple and easy to use.

BEST MODE FOR CARRYING OUT THE INVENTION

Figure 1:
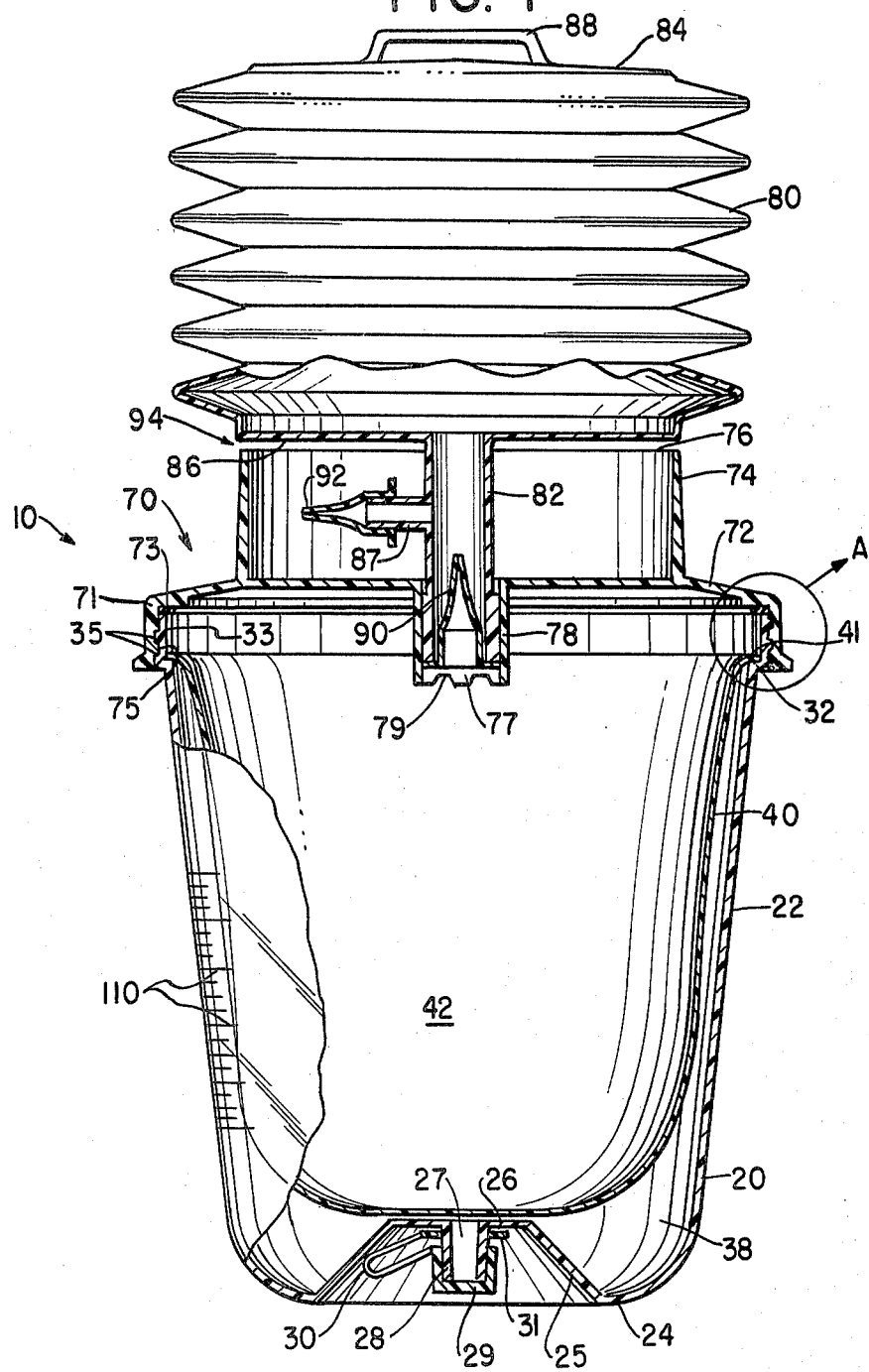
FIG. 1 is a partial cross sectional view of an exemplary embodiment of a device according to the present invention.

FIG. 1 illustrates an exemplary embodiment in vertical cross section of a device 10 according to the present invention.

Although reference herein is made to directions with respect to the device 10 as illustrated in FIG. 1, such reference is simply for the sake of convenience and is not intended to limit the device 10 in structure or operation in any way whatsoever.

The device 10 comprises a generally cylindrical rigid housing 20 having side walls 22 and an end wall 24 at one end thereof. The side walls 22 preferably are tapered toward the end wall 24. The other end of the housing 20 is open. A passive, i.e., non-elastic, member 40 is disposed within the housing 20 with its periphery 41, shown in FIG. 2, in fluid tight arrangement with an edge lip 32 of the housing 20. The passive member 40 is both expandable to a substantially fully extended state and collapsible from said bag-like extended state. In its extended state, the passive member 40 is of a dimension to substantially conform to the tapered side walls 22 of housing 22 so as to constitute a bag-like structure as shown in FIG. 1. In this manner, the passive member 40 divides the interior of housing 20 into a first chamber 38 and a second chamber 42, the purpose of which will be explained herein. The end wall 24 centrally includes a frustoconical section 25 extending toward the open end of housing 20 and terminating in a generally circular disk 26 which has an opening 27. A hollow tube 28 integral with disk 26 and extending therefrom away from the open end of housing 20 and communicatively aligned with opening 27 permits communication of the first chamber 38 with the outside of the housing 20. A cap 29, removably placable over hollow tube 28, is attached to the hollow tube 28 by a strand 30 which terminates at one end into a ring 31 that is press fitted over hollow tube 28. Thus cap 29 when in position over hollow tube 28 completely seals the first chamber 38 from the ambient outside the housing.

Figure 2:
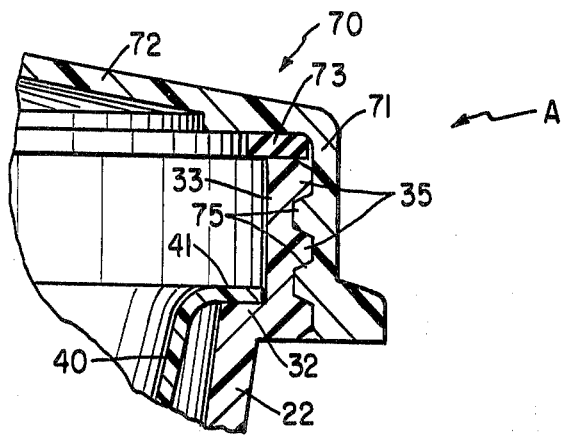
FIG. 2 is an enlarged view of a partial section of FIG. 1.

A plate member 70 is sealingly attached to the open end of housing 20 whereby the second chamber is sealed from the ambient outside the housing 20. Referring to FIG. 2, the sealing of the plate member 70 to the open end of housing 20 is shown in detail. The plate member 70 has a plate surface 72 which at its outer edges extends as a flange 71 generally transverse to plate surface 72. A circular gasket is seated as shown in FIGS. 1 and 2. A series of threads 75 on the inside surface of plate flange 71 and a cooperating series of threads 35 on the outside surface of housing flange 33 permit the screwing of plate member 70 over the open end of housing 20 as shown in FIG. 2. In this fashion, the gasket 73 provides a fluid tight seal between the bottom of plate surface 72 and the upper edge of housing flange 33.

The plate member 70 centrally has an opening 77. A hollow tube 78 integral with the plate member 70 and extending into the second chamber is communicatively aligned with the opening 77. The opening 77 of plate member 70 permits the application of a suction to the second chamber 42.

The suction can be supplied, if desired, by a remote means (not shown) by way of suitable tubing and connections (not shown) with the opening 77. Alternatively, the hollow tube 78 can extend upwardly from the outer surface of plate member 70 to accommodate suitable tubing (not shown) extending from the remote suction means.

Alternatively, the suction means is an elastic bellows 80 having a generally circular cross section and a diameter approximately that of the plate member 70. The bellows 80 has an upper surface 84 and a lower surface 86 which are substantially parallel to each other and to the plate surface 72. The lower surface 86 has centrally a hollow tube 82 which communicates with the interior of the bellows 80 and extends from the lower surface 86 into the plate tube 78 as shown in FIG. 1. The tubes 78 and 82 are suitably dimensioned to provide an air tight seal between the respective contacting tube surfaces.

When the suction force is provided by a bellows 80, the plate member 70 preferably has integral side walls 74 of a thickness approximately that of plate member 70 and of an outside diameter approximately equal to the diameter of the bellows lower surface 86. The upper edges 76 of the side walls 74 are adjacent the bellows lower surface 86 thereby creating a spaced separation 94, the purpose of which will be explained herein.

The bellows tube 82 has a hollow vent tube 87 which is integral with tube 82 and extends transversely from tube 82. Vent tube 87 is in communication with the interior of bellows tube 82 and thereby the interior of bellows 80.

A one-way valve 90 is sealingly inserted within tube 82 at its farthest end from the bellows 80 to permit entry of air from the second chamber into the bellows 80. Additionally another one-way valve 92 is sealingly inserted over tube 87 to permit air from the bellows 80 to exhaust into the ambient through the spaced separation 94.

The device 10 described above provides the user with a simple and easily operable wound suction device. Upon receipt of the device 10, the user would remove cap 29 and attach suitable wound tubing (not shown) to tube 28. The user then would compress the bellows 80 to activate the device 10. During compression, air within the bellows 80 would be expelled therefrom through bellows tube 82, vent tube 87, out one-way valve 92, and would escape through separation 94 provided as described above. Upon release of the bellows 80, the resiliency of bellows 80 will cause the bellows 80 to expand and draw air from the second chamber 42 through one way valve 90 and tube 82 into the interior of bellows 80. However, the one-way valve 92 will seal during the evacuation of air from the second chamber 42 thereby preventing drawing any ambient air into the bellows 80.

The tube 82 can be made substantially rigid so as to prevent the lower surface 86 of bellows from coming in contact with the upper edges of the side walls 74 during compression and thereby preventing the air within the bellows 80 from bleeding off into the ambient. Alternatively the side walls 74 can have perforations to permit such air bleeding.

The application of suction to the second chamber will draw the passive member 40 toward the plate member 70 and thereby collapse the passive member 40. Simultaneously the volume of the first chamber is increased whereupon a negative pressure is created therein which provides a suction force that draws bodily fluids from a wound through the conventional wound tubing into the first chamber 38.

If during the process of drawing fluids from the wound it is desired to recompress the bellows 80, the valve means provided by one-way valves 90 and 92 permit such recharging of the bellows while maintaining the present level of negative pressure then within the second chamber 42.

During the collapse of the passive member 40 within the housing 20, it is possible that the passive member could collapse across the opening of tube 78 and cut off the suction to the second chamber 42. In order to avoid this potential problem, the plate tube 78 can be provided with cutouts 79 circumferentially along the edge of tube 78. In this fashion, a path for suction to the second chamber 42 can be maintained even when the passive member 40 collapses to seal the opening of tube 78.

The housing 20 is preferably made of transparent plastic and can have etched graduations 110 thereon as shown in FIG. 1. The user will therefore be able to visibly inspect the proper operation of the device 10. Additionally he can measure the amount of fluid collected upon holding the housing 20 end wall 24 down and comparing the fluid level against the graduations 110.

Preferably the housing 20, plate member 70, and passive member 40, are made by injection molding of suitable plastic material. The bellows 80 is made by blow molding. The gasket 73 is preferably made of rubber and secured to the inside of plate surface 72 thereby providing a fluid tight seal upon securing plate member 70 to housing 20. Advantageously the housing 20 is substantially rigid thereby avoiding the possibility of inadvertent compression by a patient rolling over onto the device 10. Also the device 10 provides a self contained sealed unit upon replacing cap 28 which avoids the danger of user infection by removing the need of the user having to empty the device 10 after use. If desired, the device 10 can be safely transported by the user, e.g., to a pathology laboratory for subsequent testing of the fluids removed from a wound, also without danger of user infection.

The device 10 also provides for the avoidance of contamination of the wound with possible bacteria or the like in the ambient. The passive member 40 separates the suction means, preferably the bellows 80 whose interior at the time of charging comes into contact with the ambient, from the first chamber 38 into which the fluids are drawn. Any bacteria that may enter the second chamber 42 are kept from the first chamber 38 and thereby the wound.

The device 10 as disclosed herein is not orientation sensitive and can be utilized in any position. If desired, a loop 88 can be attached to the upper surface 84 of bellows 80 to allow attaching the device 10 to the patient. In this manner the patient is permitted free movement with the attached device 10.

The final assembly of the device 10 is not limited to the means described above. The valves 90, 92 which are respectively inserted into the tube 82 and over tube 87 to create fluid tight seals can also be glued into and over the respective tubes 82, 87. The plate member 70 instead of being screwed to the outer surface of housing flange 33 can be constructed without the need of threads 35, 75 so as to permit press fitting of plate surface 72 over housing flange 33 in fluid tight arrangement. Alternatively the plate surface 72 can be glued or ultrasonically welded to the housing flange 33. However, the passive member 40 is preferably ultrasonically or thermally welded to the edge lip 32 of housing 20. Assembly of the device 10 is not limited to gluing, press fitting, or ultrasonic welding but may be accomplished by other conventional means known and appreciated by those skilled in such arts including but not limited to mechanical means such as screws.

Figure 3:
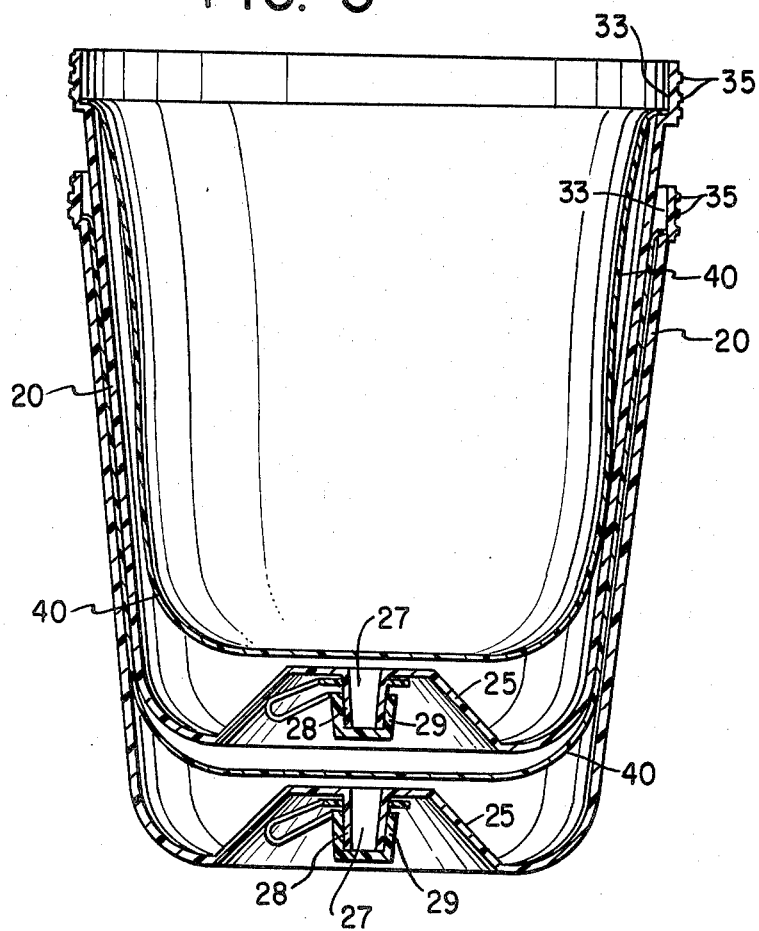
FIG. 3 is a vertical cross sectional view of a group of housings of the device in FIG. 1 in stacked array.

Referring to FIG. 3, a number of housings 20 are shown in stacked relation which is facilitated by the tapering of the housings 20 and the conforming shape of passive members 40. In this fashion the housings 20 can be conveniently stored until needed. The cap 29 over housing tube 28 maintains a sterile environment inside the first chamber 38. When needed for removal of fluids from a wound, a housing 20 is removed from the other stacked housings 20. A plate member 70 preferably with a bellows 80 is attached to the housing 20 to seal the secon chamber 42. The cap 29 is removed and conventional wound tubing (not shown) is connected to housing tube 28. The device 10 is then activated by compression of bellows 80 and fluids from a wound are drawn into the first chamber 38.

In an alternative embodiment (not shown), the disk 26 is integrally made of rubber and has a thickness which permits piercing the disk 26 with one end of a hollow thin walled needle (not shown). The disk 26 maintains a fluid tight seal about the wall of the needle in contact with the rubber of disk 26. The needle has a diameter suitable to pass body fluids into the first chamber 38. At its other end the needle is attached to conventional tubing which communicates with the wound area to be drained. In this fashion, a sterile environment is maintained in the first chamber 38 throughout the operation of connecting the device 10 to conventional wound tubing.

We claim:

1. A device for removal of exudate from a wound comprising:
   a. a housing having a first end and a second end, side walls and end walls at each of the first and the second ends, said housing defining a generally enclosed chamber, each end having an opening for communicating with said chamber;
   b. a collapsible passive non-elastic member means expandable to its original extended state having a peripheral edge and being both airtight and watertight, said passive member means being disposed within the housing and sealingly connected at its periphery adjacent proximal to the second end of the housing so as to separate the interior of the housing chamber into a first chamber portion communicating with said first end wall opening and a second chamber portion communicating with said second end wall opening, said passive member means being configured and dimensioned such that when it is substantially expanded toward the first end wall it substantially conforms to the configuration of the inside of the side walls of the housing; and
   c. bellows means disposed outside of the walls of said housing and coupled to the second end wall opening for decreasing the pressure within said second chamber portion solely by said means so as to draw and collapse the passive member means toward the second end of the housing such that the volume of the first chamber portion is increased and a negative pressure is created therein.

2. The device of claim 1 wherein said passive member means is sealingly connected at its periphery to the second end of the housing.

3. The device of claim 2 further including a means for providing communication between the first chamber and the wound from which fluids are to be removed.

4. The device of claim 3 wherein the communicating means comprises a hollow tube, said tube affixed at its one end to the end wall of the housing and communicating with the first chamber therein, whereby the first chamber is in fluid communication with the outside of the housing.

5. The device of claim 4 further including a plate member sealingly affixed to the other end of the housing thereby sealing the second chamber at the other end of the housing, said plate member having an opening communicating with the second chamber of the housing, whereby the second chamber is in communication with the outside of the housing.

6. The device of claim 5 wherein the means for drawing comprises a suction means connected to said opening of the plate member such that application of suction to said second chamber draws the passive member toward the plate member thereby increasing the volume of the first chamber and creating a negative pressure therein.

7. The device of claim 6 wherein the suction means comprises a bellows affixed to the plate member and communicatively aligned with said opening of the plate member whereby compression and releases of said bellows produces a suction force which draws the passive member toward the plate member.

8. The device of claim 7 further including a valve means providing for release of air from the bellows during compression thereof while at the same time preventing such air from entering the second chamber, thereby sealing off the second chamber during compression of the bellows.

9. The device of claim 8 wherein the housing is substantially rigid.

10. The device of claim 9 wherein the housing is substantially cylindrical.

11. The device of claim 10 wherein the side walls are tapered toward the end wall.

12. The device of claim 11 wherein the housing is a transparent plastic thereby permitting visible inspection of the operation of the passive member within the housing and the collection of fluid within the first chamber.

13. The device according to claim 12 further including graduations on the housing thereby permitting the measuring of fluid collected within the first chamber.

14. A device for removal of exudate from a portion of a living body comprising:
   a. a housing having a first end and a second end, said housing having side walls and end walls at each of the first and the second ends, said housing defining a generally enclosed interior, each end having an opening for communicating with said interior;
   b. a collapsible airtight and watertight passive non-elastic member means expandable to its original extended state having a peripheral edge, said passive member means being positioned within the housing and sealingly connected at its peripheral edge adjacent generally to the second end of the housing so as to separate the interior of the housing into a first chamber communicating with said first end opening and a second chamber communicating with said second end opening, said passive member means being configured and dimensioned such that when it is substantially expanded toward the first end wall it substantially conforms to the configuration of the inside of the side walls of the housing;
   c. a conduit communicating at one end thereof with the second end opening;

d. a bellows positioned outside of the walls of said housing and in communication with the other end of said conduit such that selective compression and expansion of the bellows produces a suction force for drawing the passive member means toward the second end of the housing solely by said suction force such that the volume of the first chamber is increased and a negative pressure created therein;

e. a first one-way valve positioned within said conduit so as to permit evacuation of the second chamber upon expansion of the bellows and to seal the second chamber during selective compression of the bellows;

f. a second one-way valve coupled with the conduit so as to permit evacuation of the bellows during compression thereof; and g. conduit means communicating with said first opening and also with the portion of a living body so as to permit the drawing of fluids therefrom as a result of the suction created by the negative pressure of the first chamber.

* * * * *

UNITED STATES PATENT AND TRADEMARK OFFICE
CERTIFICATE OF CORRECTION

PATENT NO. : 4,392,860
DATED : July 12, 1983
INVENTOR(S) : Charles M. Huck, et al.

It is certified that error appears in the above—identified patent and that said Letters Patent is hereby corrected as shown below:

On the title page add --Attorney, Agent, or Firm- Pennie & Edmonds--.

In column 1, line 17, "collect as a wound" should read --collect at a wound--.

In column 2, line 3, "th" should read --the--.

Signed and Sealed this

Eleventh Day of September 1984

[SEAL]

Attest:

GERALD J. MOSSINGHOFF

*Attesting Officer*     *Commissioner of Patents and Trademarks*